US007141035B2

(12) United States Patent
Haggstrom

(10) Patent No.: US 7,141,035 B2
(45) Date of Patent: Nov. 28, 2006

(54) CATHETER WITH OCCLUSION RESISTANT TIP

(75) Inventor: Kurt Haggstrom, Plainville, MA (US)

(73) Assignee: Sherwood Services AG, Schaffahusen (CH)

( * ) Notice: Subject to any disclaimer, the term of this patent is extended or adjusted under 35 U.S.C. 154(b) by 89 days.

(21) Appl. No.: 10/602,897

(22) Filed: Jun. 24, 2003

(65) Prior Publication Data

US 2004/0193102 A1 Sep. 30, 2004

Related U.S. Application Data

(63) Continuation-in-part of application No. PCT/US03/09687, filed on Mar. 28, 2003.

(51) Int. Cl.
*A61M 3/00* (2006.01)
(52) U.S. Cl. .................................................. 604/43
(58) Field of Classification Search ............ 604/39–43, 604/523, 528, 264, 910, 93.01
See application file for complete search history.

(56) References Cited

U.S. PATENT DOCUMENTS

| 701,075 | A | 5/1902 | McCully | |
|---|---|---|---|---|
| 2,541,691 | A | 2/1951 | Eicher | |
| D208,838 | S | 10/1967 | St. Amand | D83/1 |
| 4,134,402 | A | 1/1979 | Mahurkar | 128/214 R |
| D254,270 | S | 2/1980 | Ziegler | D24/23 |
| 4,385,631 | A * | 5/1983 | Uthmann | 604/284 |
| D272,651 | S | 2/1984 | Mahurkar | D24/54 |
| 4,443,333 | A | 4/1984 | Mahurkar | 210/87 |
| 4,568,329 | A | 2/1986 | Mahurkar | 604/43 |
| 4,583,968 | A * | 4/1986 | Mahurkar | 604/43 |
| 4,601,697 | A | 7/1986 | Mammolenti et al. | 604/43 |
| 4,604,379 | A | 8/1986 | Twardowski et al. | 514/21 |
| D289,682 | S | 5/1987 | Dragan | D24/16 |
| 4,675,004 | A | 6/1987 | Hadford et al. | 604/44 |
| 4,682,978 | A | 7/1987 | Martin | 604/43 |
| 4,687,471 | A | 8/1987 | Twardowski et al. | 604/175 |
| 4,692,141 | A | 9/1987 | Mahurkar | 604/43 |
| D292,825 | S | 11/1987 | Dragan | D24/16 |
| 4,770,652 | A | 9/1988 | Mahurkar | 604/4 |
| 4,772,269 | A | 9/1988 | Twardowski et al. | 604/175 |
| D298,461 | S | 11/1988 | Manno | D24/51 |
| 4,808,155 | A | 2/1989 | Mahurkar | 604/43 |
| 4,842,582 | A | 6/1989 | Mahurkar | 604/43 |

(Continued)

FOREIGN PATENT DOCUMENTS

EP          0107810          5/1984

(Continued)

*Primary Examiner*—Nicholas Lucchesi
*Assistant Examiner*—Theodore J. Stigell
(74) *Attorney, Agent, or Firm*—Carter, DeLuca, Farrell & Schmidt LLP

(57) ABSTRACT

A catheter is provided that includes an elongated tubular body extending to a distal end. The tubular body has a first and a second lumen with a septum disposed therebetween. The tubular body includes a first wall that defines the first lumen and a second wall that defines the second lumen. A portion of the septum extends distally beyond the first lumen and the second lumen. The first wall includes a first wall extension that extends distally beyond the first lumen and is spaced apart from the portion of the septum. The first wall extension defines a concave surface facing the portion of the septum. Alternatively, the septum has a septum extension that extends distally beyond the first lumen and the second lumen. In alternate embodiment, the septum extension defines a first planar surface and an opposing second planar surface.

19 Claims, 14 Drawing Sheets

U.S. PATENT DOCUMENTS

| | | | | |
|---|---|---|---|---|
| 4,883,426 A | | 11/1989 | Ferrer | 433/91 |
| 4,895,561 A | | 1/1990 | Mahurkar | 604/43 |
| 4,904,238 A | | 2/1990 | Williams | 604/43 |
| D312,872 S | | 12/1990 | Mähl | D24/10 |
| 5,009,636 A | | 4/1991 | Wortley et al. | 604/43 |
| 5,015,184 A | | 5/1991 | Perry et al. | 433/93 |
| 5,057,073 A | * | 10/1991 | Martin | 604/43 |
| 5,171,227 A | | 12/1992 | Twardowski et al. | 604/175 |
| 5,197,951 A | | 3/1993 | Mahurkar | 604/93 |
| 5,209,723 A | | 5/1993 | Twardowski et al. | 604/43 |
| 5,221,255 A | | 6/1993 | Mahurkar | 604/43 |
| 5,221,256 A | | 6/1993 | Mahurkar | 604/43 |
| 5,273,527 A | | 12/1993 | Schatz et al. | 604/43 |
| 5,281,134 A | | 1/1994 | Schultz | 433/29 |
| 5,282,788 A | | 2/1994 | Wilk et al. | 604/49 |
| 5,290,282 A | | 3/1994 | Casscells | 606/29 |
| 5,318,518 A | * | 6/1994 | Plechinger et al. | 604/43 |
| 5,336,165 A | | 8/1994 | Twardowski | 604/5 |
| 5,374,245 A | * | 12/1994 | Mahurkar | 604/43 |
| 5,378,230 A | | 1/1995 | Mahurkar | 604/43 |
| 5,403,291 A | | 4/1995 | Abrahamson | 604/280 |
| 5,405,320 A | | 4/1995 | Twardowski et al. | 604/43 |
| 5,405,341 A | | 4/1995 | Martin | 604/284 |
| 5,419,777 A | | 5/1995 | Hofling | 604/264 |
| 5,451,216 A | * | 9/1995 | Quinn | 604/270 |
| 5,464,398 A | | 11/1995 | Haindl | 604/280 |
| 5,484,397 A | | 1/1996 | Twardowski | 604/5 |
| 5,486,159 A | | 1/1996 | Mahurkar | 604/4 |
| 5,509,897 A | | 4/1996 | Twardowski et al. | 604/43 |
| 5,522,807 A | * | 6/1996 | Luther | 604/264 |
| 5,536,234 A | | 7/1996 | Newman | 600/104 |
| 5,549,541 A | | 8/1996 | Muller | 600/105 |
| 5,554,136 A | | 9/1996 | Luther | 604/264 |
| 5,562,640 A | | 10/1996 | McCabe et al. | 604/280 |
| 5,569,182 A | * | 10/1996 | Twardowski et al. | 604/43 |
| 5,571,093 A | * | 11/1996 | Cruz et al. | 604/270 |
| 5,607,440 A | | 3/1997 | Danks et al. | 606/185 |
| 5,685,867 A | * | 11/1997 | Twardowski et al. | 604/523 |
| 5,707,351 A | | 1/1998 | Dorsey, III | 604/30 |
| 5,725,495 A | | 3/1998 | Strukel et al. | 604/44 |
| 5,776,092 A | | 7/1998 | Farin et al. | 604/22 |
| 5,782,797 A | | 7/1998 | Schweich, Jr. et al. | 604/49 |
| 5,785,678 A | * | 7/1998 | Griep et al. | 604/28 |
| 5,788,680 A | | 8/1998 | Linder | 604/280 |
| 5,788,681 A | | 8/1998 | Weaver et al. | 604/280 |
| 5,801,012 A | | 9/1998 | Soff et al. | 435/68.1 |
| 5,830,196 A | | 11/1998 | Hicks | 604/280 |
| 5,858,009 A | | 1/1999 | Jonkman | 604/264 |
| 5,902,476 A | | 5/1999 | Twardowski | 210/143 |
| 5,961,486 A | * | 10/1999 | Twardowski et al. | 604/43 |
| 6,063,099 A | | 5/2000 | Danks et al. | 606/185 |
| 6,086,565 A | | 7/2000 | Ouchi | 604/187 |
| 6,126,631 A | | 10/2000 | Loggie | 604/43 |
| 6,132,616 A | | 10/2000 | Twardowski et al. | 210/646 |
| 6,146,536 A | | 11/2000 | Twardowski | 210/646 |
| 6,152,910 A | | 11/2000 | Agro et al. | 604/523 |
| 6,190,357 B1 | | 2/2001 | Ferrari et al. | 604/102.01 |
| 6,299,444 B1 | | 10/2001 | Cohen | 433/91 |
| 6,409,700 B1 | * | 6/2002 | Siegel et al. | 604/43 |
| 6,423,050 B1 | | 7/2002 | Twardowski | 604/500 |
| 6,428,502 B1 | | 8/2002 | Lang | 604/28 |
| 6,461,321 B1 | * | 10/2002 | Quinn | 604/43 |
| 6,517,529 B1 | * | 2/2003 | Quinn | 604/528 |
| 6,540,714 B1 | * | 4/2003 | Quinn | 604/43 |
| 6,576,609 B1 | | 6/2003 | Soff et al. | 514/12 |
| 6,592,565 B1 | | 7/2003 | Twardowski | 604/500 |
| 6,702,776 B1 | * | 3/2004 | Quinn | 604/43 |
| 6,786,884 B1 | * | 9/2004 | DeCant et al. | 604/43 |

FOREIGN PATENT DOCUMENTS

| | | |
|---|---|---|
| EP | 0341721 | 11/1989 |
| EP | 0555780 | 8/1993 |
| EP | 0623356 | 11/1994 |
| GB | 2028136 | 3/1980 |
| WO | WO 95/10317 | 4/1995 |

* cited by examiner

CATHETER WITH OCCLUSION RESISTANT TIP

RELATED APPLICATION INFORMATION

This patent application is a continuation-in-part of PCT International Application No. PCT/US03/09687, filed on Mar. 28, 2003 designating the United States of America, the entire contents of which is incorporated herein by reference.

BACKGROUND

1. Technical Field

The present disclosure relates generally to medical catheter apparatus, and more particularly to a catheter including a catheter tip that prevents occlusion during use.

2. Description of the Related Art

Some known catheters are tubular, flexible medical devices for administration of fluids (withdrawal, introduction, etc.) within cavities, ducts, vessels, etc. of a body.

These catheter devices may be employed for administration of fluids that includes the simultaneous introduction and withdrawal of fluid for applications such as, surgery, treatment, diagnosis, etc. In one particular hemodialysis application, blood is withdrawn from a blood vessel for treatment by an artificial kidney device and the treated blood is introduced back into the blood vessel.

Various known catheter devices have been employed for simultaneous withdrawal and introduction of fluid with a body. These devices may utilize multiple lumens, such as dual lumen catheters that facilitate bidirectional fluid flow whereby one lumen performs withdrawal of blood and the other lumen introduces treated blood to the vessel. During an exemplary hemodialysis procedure, a multiple lumen catheter is inserted into a body and blood is withdrawn through an arterial lumen of the catheter. This blood is supplied to a hemodialysis unit which dialyzes, or cleans, the blood to remove waste and excess water. The dialyzed blood is returned to the patient through a venous lumen of the catheter. Typically, the venous lumen is separated from the arterial lumen by an inner catheter wall, called a septum.

The efficiency of a hemodialysis procedure may be reduced by undesirable recirculation of blood flow whereby the dialyzed blood exiting the venous lumen is directly returned to the arterial lumen. To overcome this drawback some catheter devices stagger the openings of the lumens such that the opening of the venous lumen is disposed distally beyond the opening of the arterial lumen.

These catheter devices, however, also suffer from various additional drawbacks. For example, blood clots can form adjacent to or on the opening of both lumens and at locations between the openings of the lumens. Another drawback that may arise, due to the dedicated flow direction for a particular lumen, is recirculation if the flow direction is reversed. Further, suction introduced through lumen openings of the prior art may draw portions of a body vessel wall therein. These drawbacks can disadvantageously result in flow occlusion.

Therefore, it would be desirable to overcome the disadvantages and drawbacks of the prior art with a catheter including a catheter tip that prevents occlusion during use to facilitate unobstructed fluid flow. It would be desirable if such a catheter included concave surfaces adjacent the catheter tip to prevent occlusion and undesirable recirculation. The catheter may also facilitate reversible flow between lumens of the catheter. It would be highly desirable if the catheter and its constituent parts are easily and efficiently manufactured and assembled.

SUMMARY

Accordingly, a catheter is provided including a catheter tip that prevents occlusion during use to facilitate unobstructed fluid flow to overcome the disadvantages and drawbacks of the prior art. Desirably, such a catheter includes concave surfaces adjacent the catheter tip to prevent occlusion and undesirable recirculation. The catheter may also facilitate reversible flow between lumens of the catheter. Most desirably, the catheter is easily and efficiently manufactured and assembled. The present disclosure resolves related disadvantages and drawbacks experienced in the art.

The present disclosure provides, among other things, a multiple lumen dialysis catheter with a tip configuration such that the distal ends of the lumens terminate in symmetrical angled relationships. Distal wall extensions of the lumens are at the same longitudinal position along the catheter. The catheter may include sideholes.

Thus, the catheter tip configuration of the present disclosure advantageously reduces the potential for positional occlusion. The design of the catheter tip helps to keep the tip away from the sidewall of the vessel, eliminating the potential for the catheter to adhere to the vessel wall when suction is applied.

The symmetrical catheter tip design also advantageously facilitates the capability of bi-directional fluid flow for each lumen of the catheter. The symmetrical configuration of the catheter tip overcomes the disadvantages of dedicating a particular lumen to a flow direction, such as, for example, inflow, outflow, etc. This configuration results in similar recirculation in either direction of the blood flow (inflow lumen used for inflow and outflow lumen used for outflow, or outflow lumen used for inflow and inflow lumen used for outflow). Thus, blood clots attached to the catheter, including the septum may be washed away by alternating and/or reversing flow directions with consecutive dialysis. It is contemplated that the alternating and/or reversible flow may be provided by a source outside the body of the catheter such as, for example, a dialysis machine, etc. connected thereto.

In one particular embodiment, a catheter is provided, in accordance with the principles of the present disclosure. The catheter includes an elongated tubular body extending to a distal end thereof. The tubular body has a first lumen and a second lumen with a septum disposed therebetween. The tubular body includes a first wall that defines the first lumen and a second wall that defines the second lumen. A portion of the septum extending distally beyond the first lumen and the second lumen. The first wall includes a first wall extension that extends distally beyond the first lumen and is spaced apart from the portion of the septum. The first wall extension defines a concave surface facing the portion of the septum.

The portion of the septum may define a planar surface that faces the concave surface of the first wall extension. The first wall extension may include a planar end surface that forms a boundary about the concave surface of the first wall extension. The planar end surface can be disposed at an angular orientation relative to a planar surface of the portion of the septum that faces the concave surface of the first wall extension.

Alternatively, the second wall includes a second wall extension that extends distally beyond the second lumen and is spaced apart from the portion of the septum. The second wall extension defines a concave surface facing the portion of the septum. The portion of the septum may define a planar surface that faces the concave surface of the second wall extension. The second wall extension may include a planar end surface that forms a boundary about the concave surface of the second wall extension. The planar end surface can be disposed at an angular orientation relative to a planar surface of the portion of the septum that faces the concave surface of the second wall extension.

The concave surface of the first wall extension may define a first cavity and the concave surface of the second wall extension may define a second cavity. The first cavity and the second cavity are symmetrical. The first wall extension and the second wall extension may be symmetrically disposed about the portion of the septum. The first wall extension may include a first step extending a first distance beyond the first lumen and a second step extending a second distance beyond the first lumen. The second wall extension may include a first step extending a first distance beyond the second lumen and a second step extending a second distance beyond the second lumen.

In an alternate embodiment, the septum has a septum extension disposed adjacent to a distal tip of the catheter and extends distally beyond the first lumen and the second lumen. The first wall extends distally beyond the first lumen and is spaced apart from the septum extension. The first wall extension defines a concave surface facing the septum extension. The second wall extends distally beyond the second lumen and is spaced apart from the septum extension. The second wall extension defines a concave surface facing the septum extension.

In another alternate embodiment, the septum extension defines a first planar surface and an opposing second planar surface. The first wall includes a first wall extension that extends distally beyond the first lumen and the second lumen. The first wall is spaced apart from the septum extension. The first wall extension defines a concave surface facing the first planar surface of the septum extension and is bounded by a planar end surface of the first wall extension. The planar end surface of the first wall extension is disposed at an angular orientation relative to the first planar surface of the septum extension. The second wall includes a second wall extension that extends distally beyond the first lumen and the second lumen. The second wall is spaced apart from the septum extension. The second wall extension defines a concave surface facing the second planar surface of the septum extension and is bounded by a planar end surface of the second wall extension. The planar end surface of the second wall extension is disposed at an angular orientation relative to the second planar surface of the septum extension.

In another alternate embodiment, the concave surface of the first wall extension defines a first cavity and the concave surface of the second wall extension defines a second cavity. The first wall extension includes a first base that defines an inlet opening of the first cavity. The first base is disposed proximal to fluid flow being expelled from the second cavity of the second wall extension. The second wall extension may include a second base that defines an inlet opening of the second cavity. The second base is disposed proximal to fluid flow being expelled from the first cavity of the second wall extension. The first base and/or the second base may have an arcuate configuration.

In another alternate embodiment, the first wall includes a first wall extension that extends in a spiral configuration from the first lumen and is spaced apart from the portion of the septum. The second wall may include a second wall extension that extends in a spiral configuration from the second lumen and is spaced apart from the portion of the septum. The first wall extension may include a planar end surface that forms a boundary about the first wall extension and defines the spiral configuration of the first wall extension. The second wall extension may include a planar end surface that forms a boundary about the second wall extension and defines the spiral configuration of the second wall extension.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

DETAILED DESCRIPTION OF THE EXEMPLARY EMBODIMENTS

Figure 1:
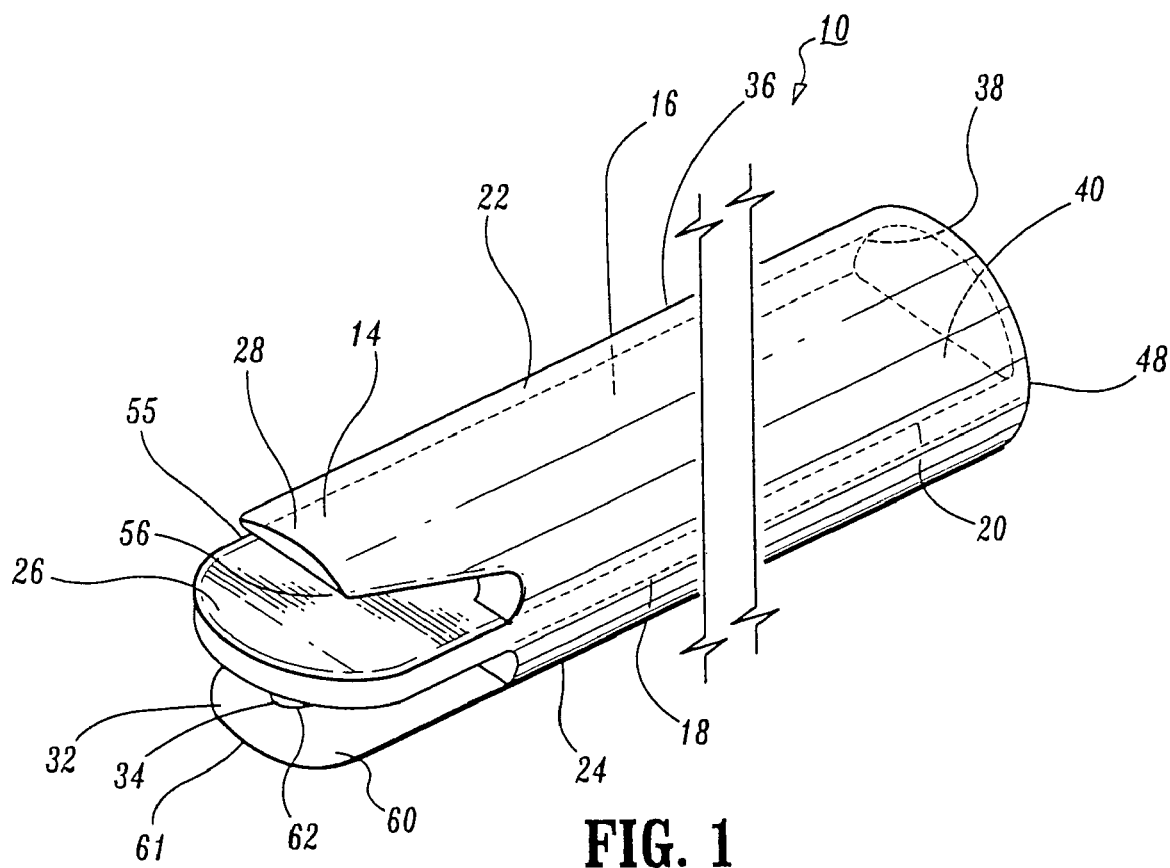
FIG. 1 is a perspective view of a catheter in accordance with the principles of the present disclosure, showing a septum in phantom.
Figure 2:
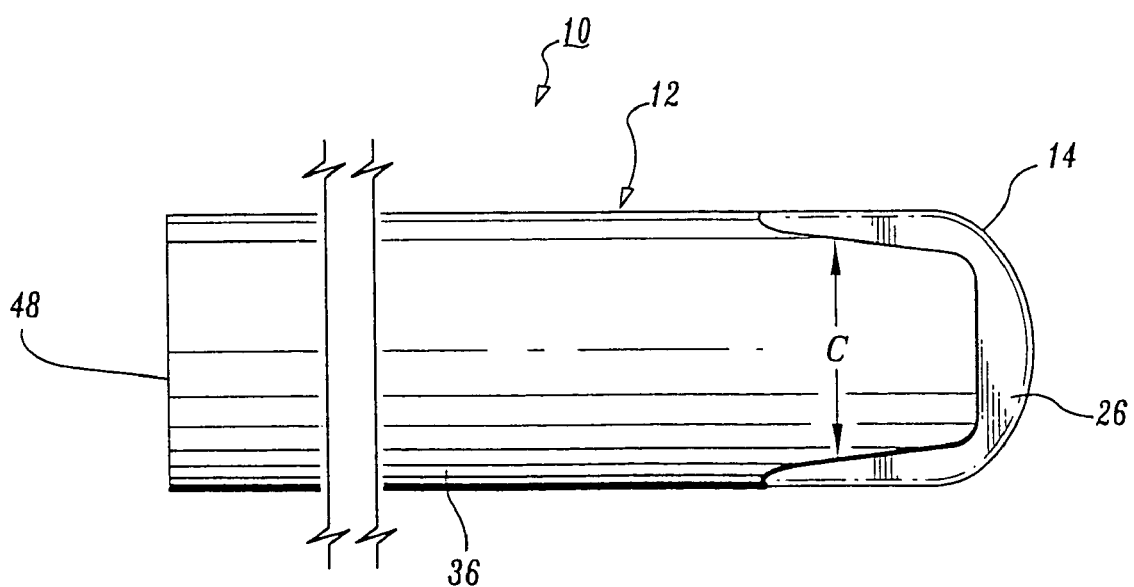
FIG. 2 is a side view of a distal end of the catheter shown in FIG. 1.
Figures 3, 4:
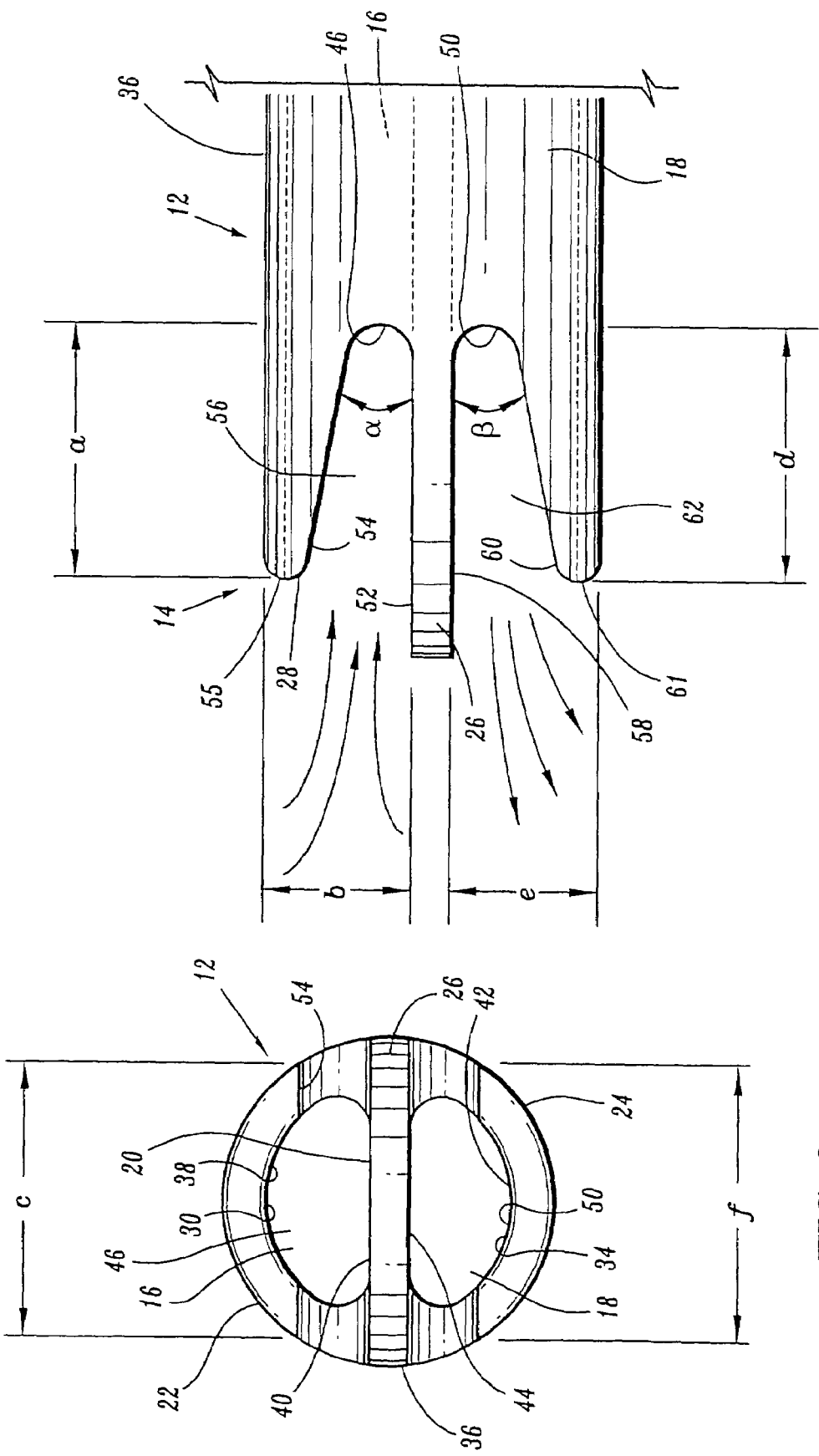
FIG. 3 is a front view of the catheter shown in FIG. 1.
FIG. 4 is an enlarged side view of the distal end of the catheter shown in FIG. 1.

The exemplary embodiments of the catheter and methods of use disclosed are discussed in terms of medical catheters for the administration of fluids (withdrawal, introduction, etc.) with the body of a subject and more particularly, in terms of a catheter including a catheter tip that prevents occlusion during use to facilitate unobstructed fluid flow. The catheter is advantageously configured to facilitate reversible fluid flow between lumens thereof. It is envisioned that the present disclosure may be employed with a range of catheters, such as, for example, hemodialysis, peritoneal, infusion, PICC, CVC, port, etc. and catheter applications including surgical, diagnostic and related treatments of diseases, body ailments, etc. of a subject. It is further envisioned that the principles relating to the catheter disclosed include employment with various catheter related procedures, such as, for example, hemodialysis, cardiac, abdominal, urinary, intestinal, etc., in chronic, acute, etc. applications. It is contemplated that the catheter can be used for administration of fluids such as, for example, medication, saline, bodily fluids such as, blood, urine, etc. The catheter may also be used to monitor subject condition.

In the discussion that follows, the term "proximal" will refer to the portion of a structure that is closer to a practitioner, while the term "distal" will refer to the portion that is further from the practitioner. As used herein, the term "subject" refers to a human patient or other animal. According to the present disclosure, the term "practitioner" refers to a doctor, nurse or other care provider and may include support personnel.

The following discussion includes a description of the catheter, in accordance with the principles of the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–4, a catheter 10 includes an elongated tubular body 12 that extends to a distal end 14. Body 12 has a first lumen 16 and a second lumen 18, with a septum 20 disposed therebetween. Body 12 includes a first wall 22 that defines first lumen 16 and a second wall 24 that defines second lumen 18. A portion, such as, for example, septum extension 26 of septum 20 extends distally beyond first lumen 16 and second lumen 18. Septum 20 is medially disposed, along a substantial portion of the longitudinal length of body 12, between first lumen 16 and second lumen 18. Septum 20 may be variously disposed with body 12, such as, for example, angularly offset relative to extended portions of the first and second walls, etc.

First wall 22 includes a first wall extension 28 that extends distally beyond first lumen 16 and is spaced apart from septum extension 26. First wall extension 28 defines a concave surface 30 that faces septum extension 26. Second wall 24 includes a second wall extension 32 that extends distally beyond second lumen 18 and is spaced apart from septum extension 26. Second wall extension 32 defines a concave surface 34 that faces septum extension 26.

Septum extension 26 extends beyond first wall extension 28 and second wall extension 32. Septum extension 26 is medially disposed, as extending from body 12, between first wall extension 28 and second wall extension 32. Septum extension 26 may be variously disposed for extension from body 12. The disclosed configuration of catheter 10 advantageously prevents occlusion of first lumen 16 and second lumen 18, as will be discussed. One or a plurality of wall extensions may be employed with catheter 10, according to the particular requirements of a catheter application.

Body 12 has a cylindrical outer surface 36. It is contemplated that body 12 may be variously dimensioned and attachable to other medical devices. It is further contemplated that outer surface 36 may have various cross-sectional configurations, such as, for example, oval, rectangular, elliptical, polygonal, etc. Body 12 may also include lateral openings. First wall 22 has a wall surface 38 that defines first lumen 16 in cooperation with a surface 40 of septum 20. Second wall 24 has a wall surface 42 that defines second lumen 18 in cooperation with a surface 44 of septum 20.

Lumens 16, 18 each may have a substantially D-shaped or semi-circular configuration. Lumens 16, 18 are elongated with body 12 and surfaces 38, 40, 42, 44 are configured to facilitate fluid flow within lumens 16, 18. It is contemplated that lumens 16, 18 may be configured for arterial and/or venous flow. It is envisioned that lumens 16, 18 may have various configurations, such as, for example, cylindrical, rectangular, elliptical, polygonal, etc. The first and second lumens may be configured for various forms of fluid flow in various directions and orientations, according to the requirements of a particular catheter application.

Lumens 16, 18 may be uniformly dimensioned or include alternative dimensional cross sections within body 12, such as, narrow and broad portions, converging surfaces, undulating surfaces, etc. according to the particular flow indications and/or flow rate requirements. It is contemplated lumen 16 and lumen 18 may extend alternative lengths. It is further contemplated that body 12 may include one or a plurality of lumens, such as, for example, a triple lumen configuration, etc.

First lumen 16 includes a first opening, such as, for example, an inlet opening 46 that is disposed adjacent to distal end 14 of body 12. An outlet opening (not shown) of first lumen 16 is disposed adjacent a proximal end 48 of body 12. Inlet opening 46 is configured for suction and may be inserted with a blood vessel of a subject (not shown) such that blood is withdrawn, by for example, arterial blood flow in a first direction, from the blood vessel for treatment by an artificial kidney device (not shown). Inlet opening 46 may be variously dimensioned and configured, such as, for example, rectangular, elliptical, polygonal, etc. and may include adapters, clips, etc. to facilitate fluid flow and/or attachment to other structure. It is contemplated that inlet opening 46 may be configured for expulsion of fluid.

First lumen 16 is separated from second lumen 18 by septum 20. Second lumen 18 includes a second opening, such as, for example, an outlet opening 50 that is disposed adjacent to distal end 14 and in substantial longitudinal alignment, along body 12, with inlet opening 46. An inlet opening (not shown) of second lumen 18 is disposed adjacent proximal end 48. Outlet opening 50 is configured for expulsion of fluid and introduces the treated blood from the artificial kidney device back into the blood vessel, by for example, venous blood flow in a second opposite direction. Outlet opening 50 may be variously dimensioned and configured, such as, for example, rectangular, elliptical, polygonal, etc. and may include adapters, clips, etc. to facilitate fluid flow and/or attachment to other structure. It is contemplated that outlet opening 50 may be configured for withdrawal of fluid.

The components of catheter 10 are fabricated from materials suitable for medical applications, such as, for example, polymerics or metals, such as stainless steel, depending on the particular catheter application and/or preference of a practitioner. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

First wall extension 28 extends distally, a distance a, beyond inlet opening 46 of first lumen 16 and outlet opening 50 of second lumen 18. It is contemplated that distance a may extend various lengths according to the requirements of a particular catheter application, such as, for example, approximately 0.100–0.200 inches. Concave surface 30 faces a first planar surface 52 of septum extension 26 and is spaced apart therefrom a distance b. It is contemplated that distance b may extend various lengths. It is further contemplated that surface 52 may be non-planar, such as, for example, arcuate, undulating, textured, etc.

Figure 5:
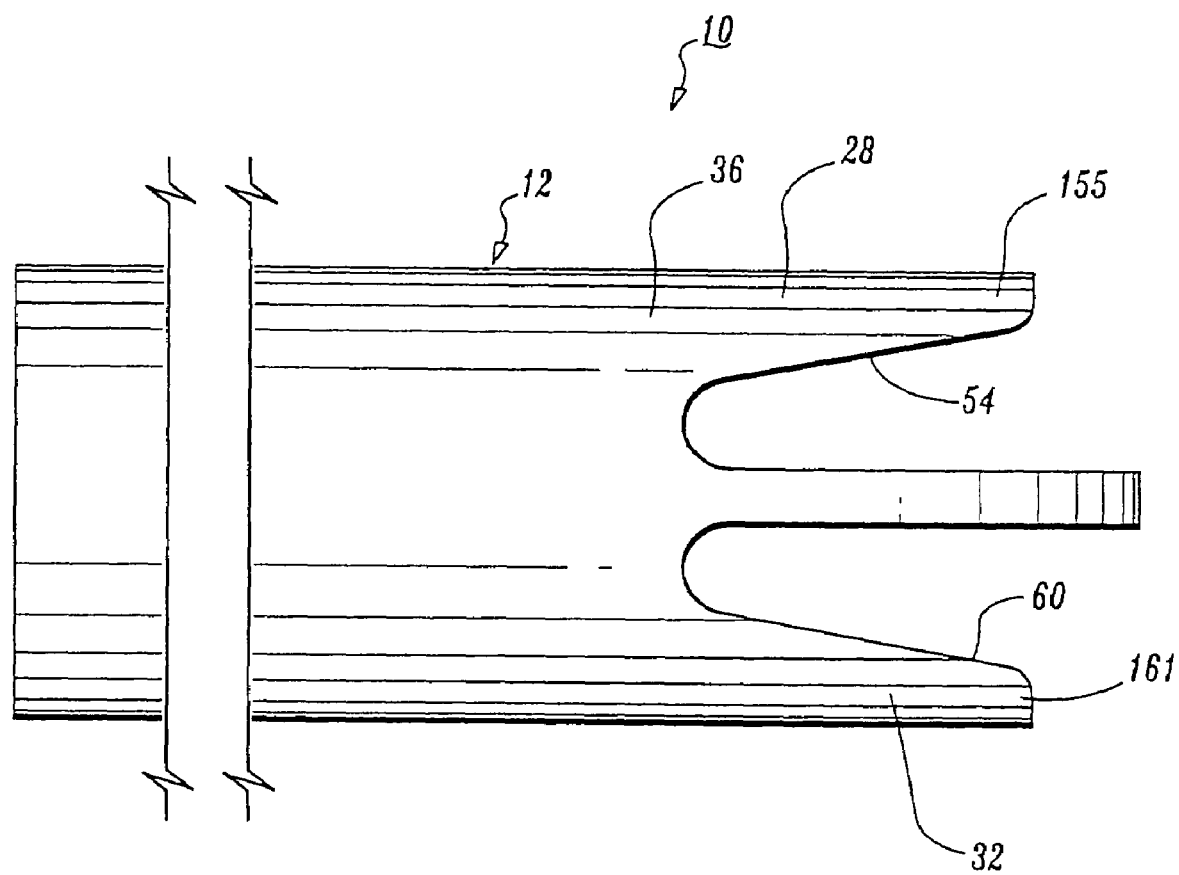
FIG. 5 is an enlarged side view of an alternate embodiment of the distal end of the catheter shown in FIG. 1.
Figures 6, 7:
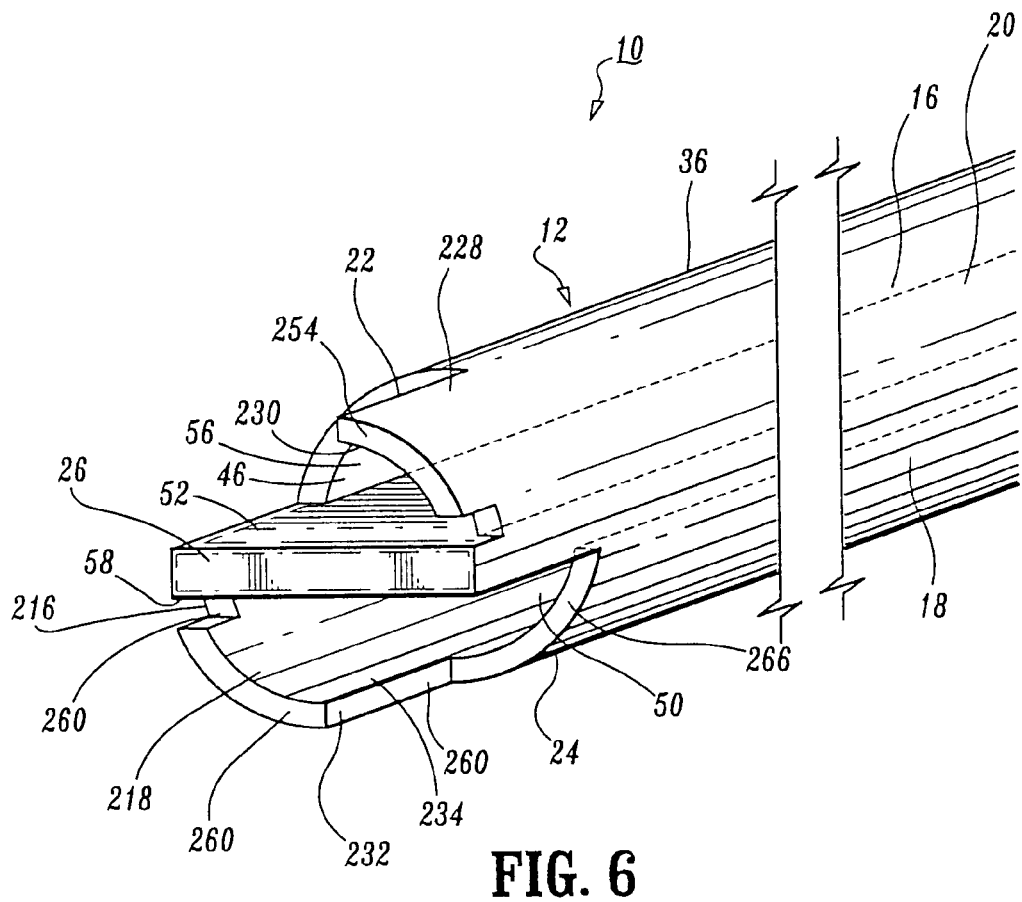
FIG. 6 is an enlarged perspective view of another alternate embodiment of the catheter shown in FIG. 1.
FIG. 7 is an enlarged alternate perspective view of the catheter shown in FIG. 6.
Figure 8:
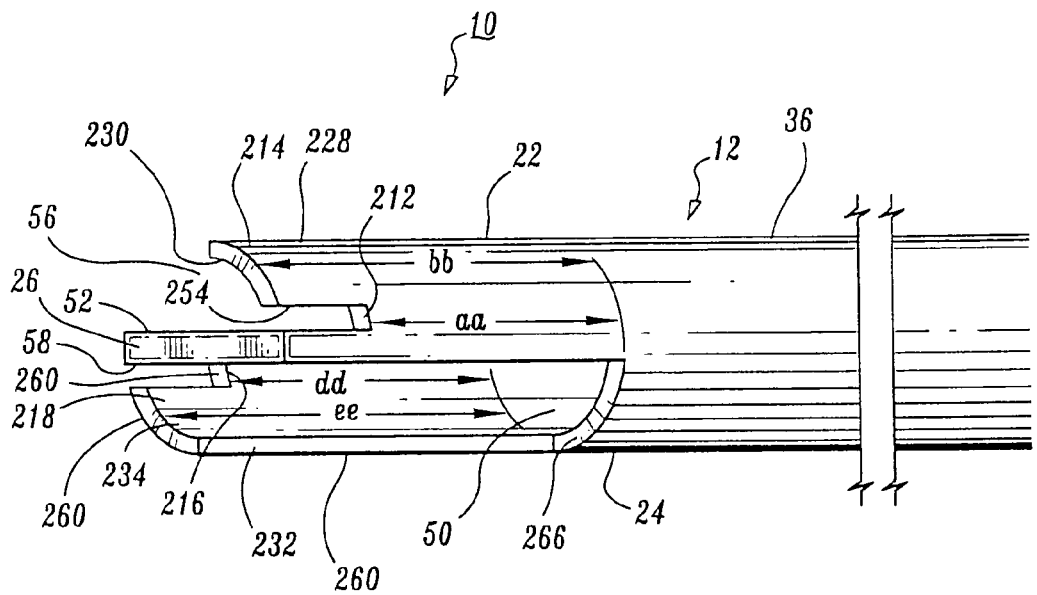
FIG. 8 is an enlarged alternate perspective view of the catheter shown in FIG. 6.
Figure 9:
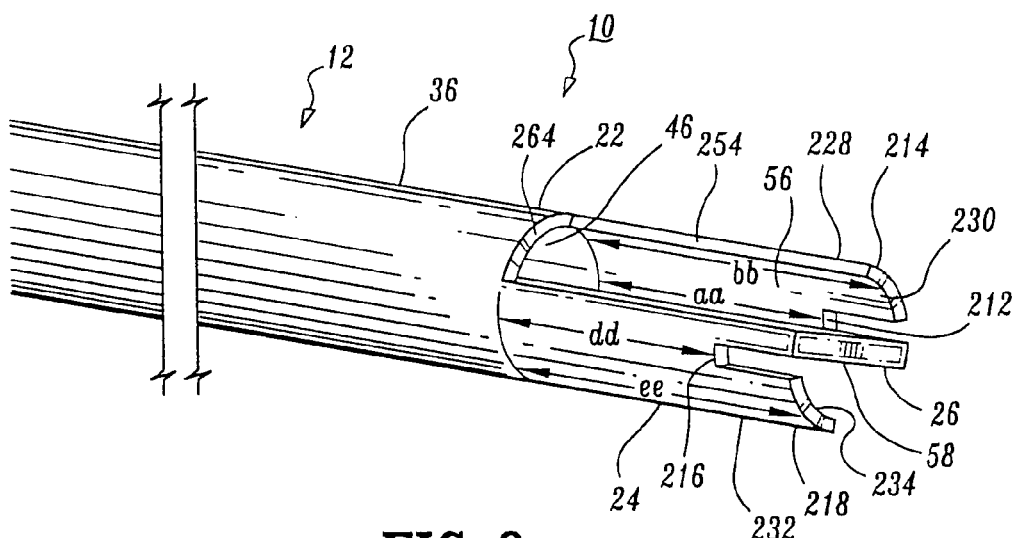
FIG. 9 is an enlarged alternate perspective view of the catheter shown in FIG. 6.
Figure 10:
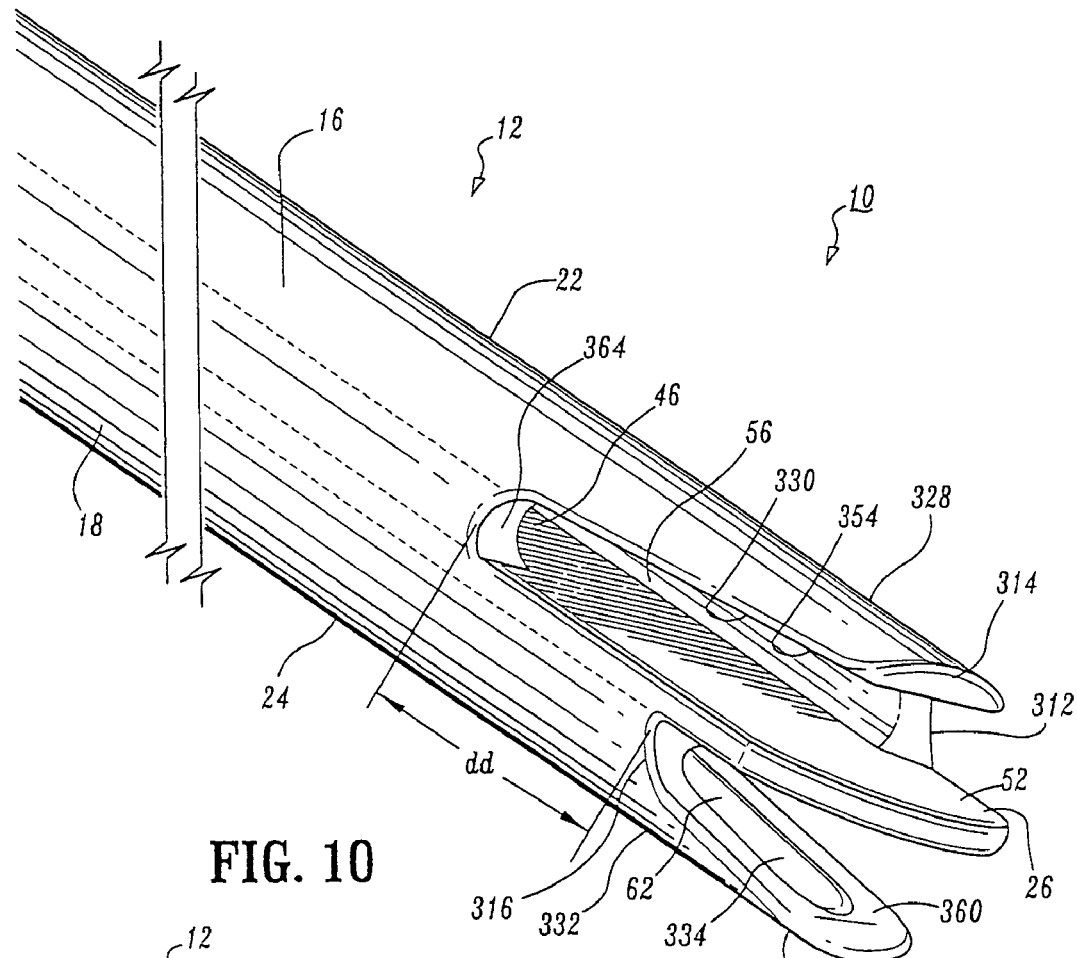
FIG. 10 is a perspective view of another alternate embodiment of the catheter shown in FIG. 1.
Figure 11:
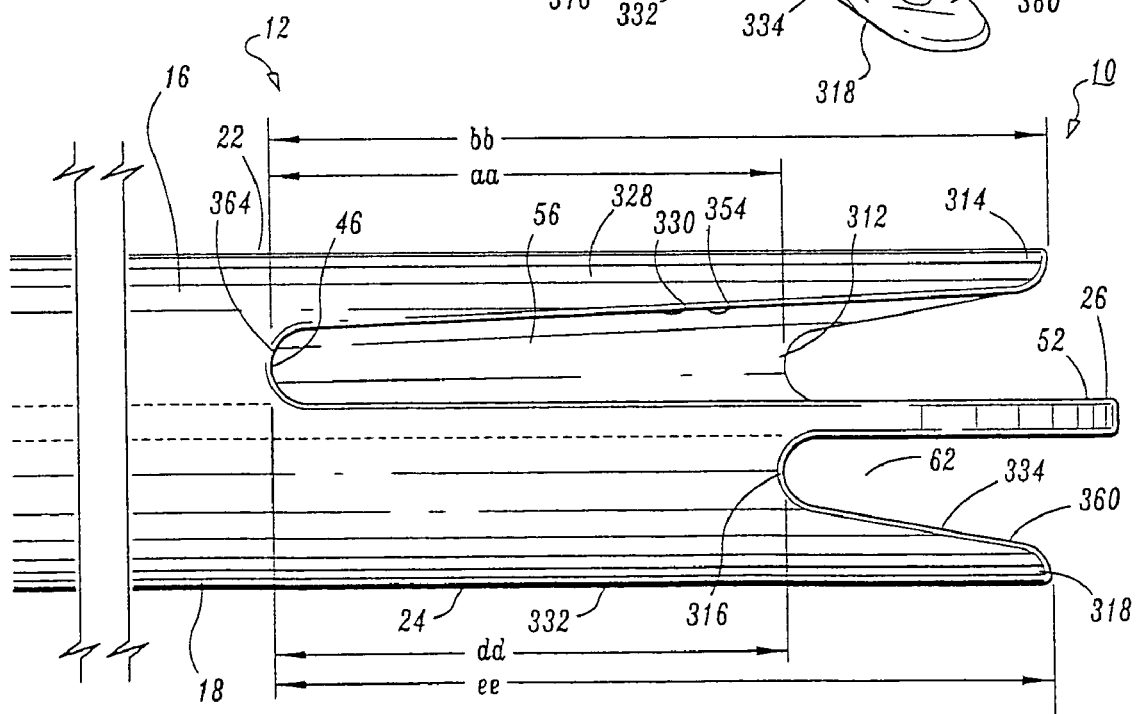
FIG. 11 is a side view of the catheter shown in FIG. 10.
Figure 12:
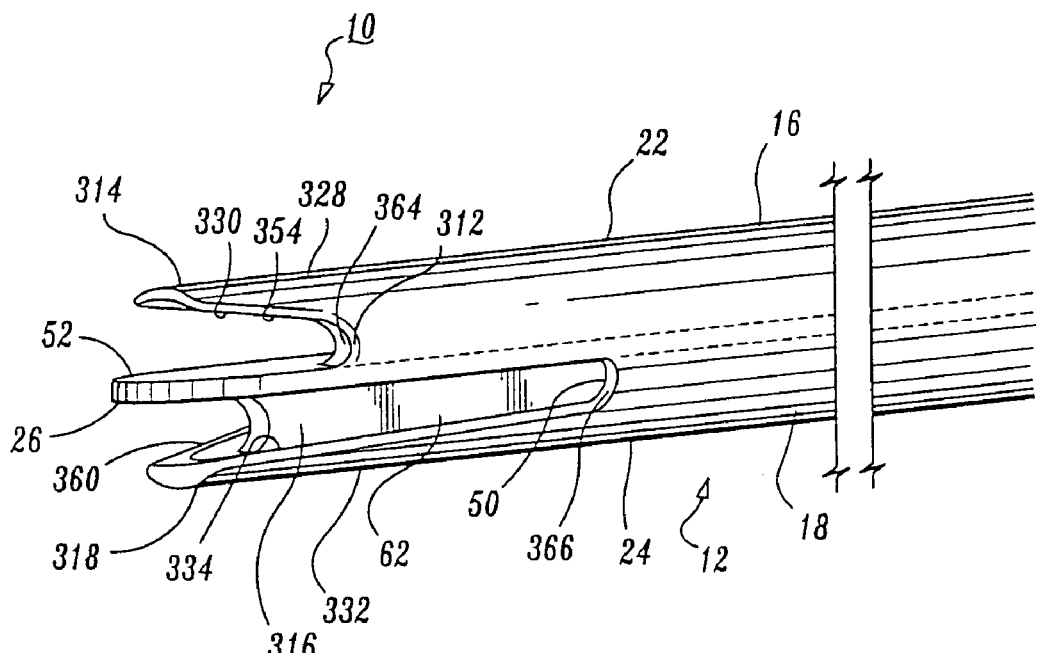
FIG. 12 is an alternate perspective view of the catheter shown in FIG. 10.
Figure 13:
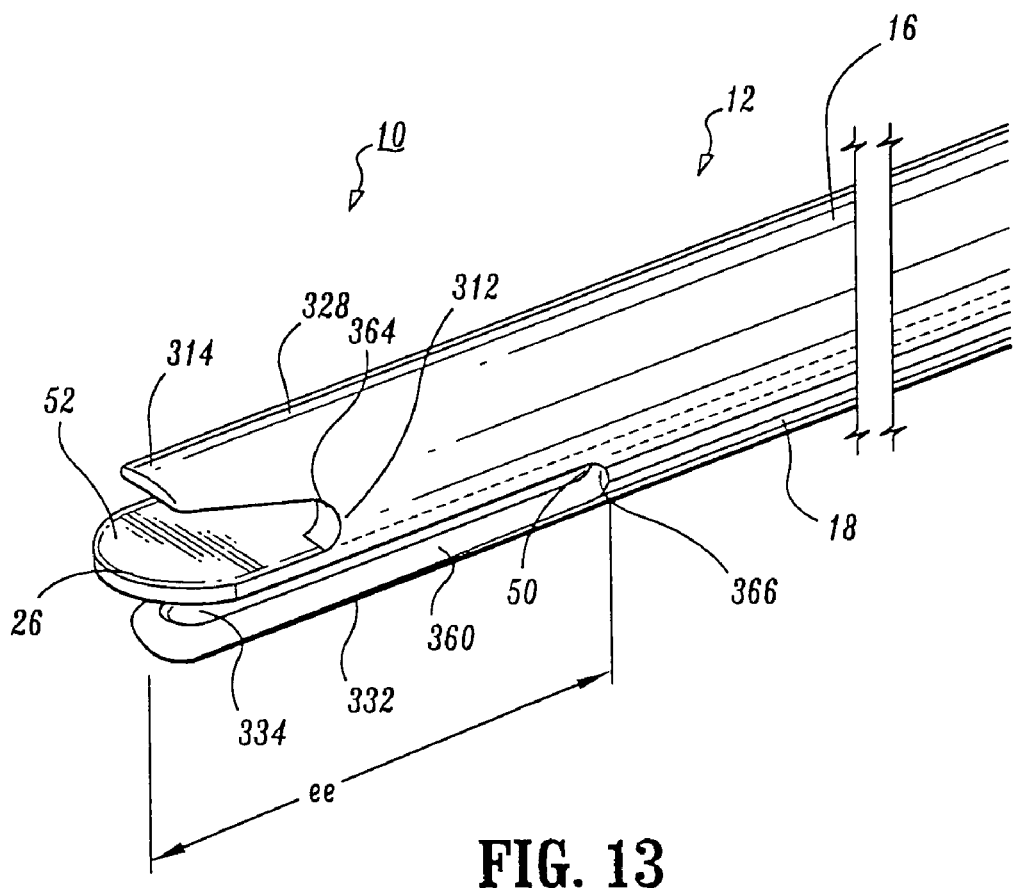
FIG. 13 is an alternate perspective view of the catheter shown in FIG. 10.
Figure 14:
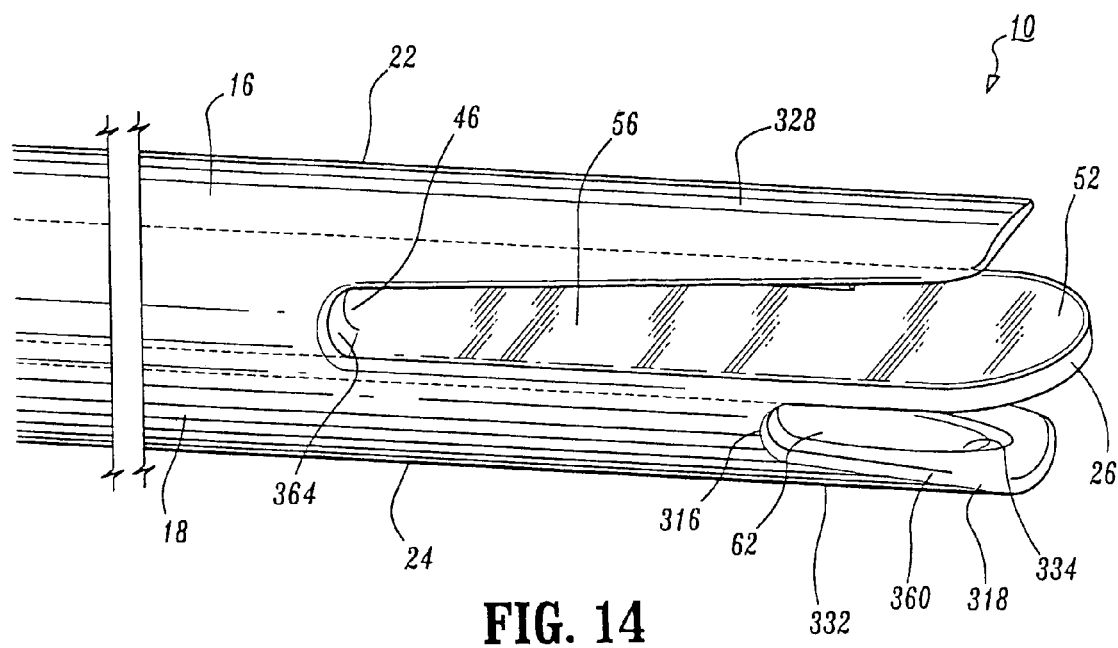
FIG. 14 is an alternate perspective view of the catheter shown in FIG. 10.
Figure 15:
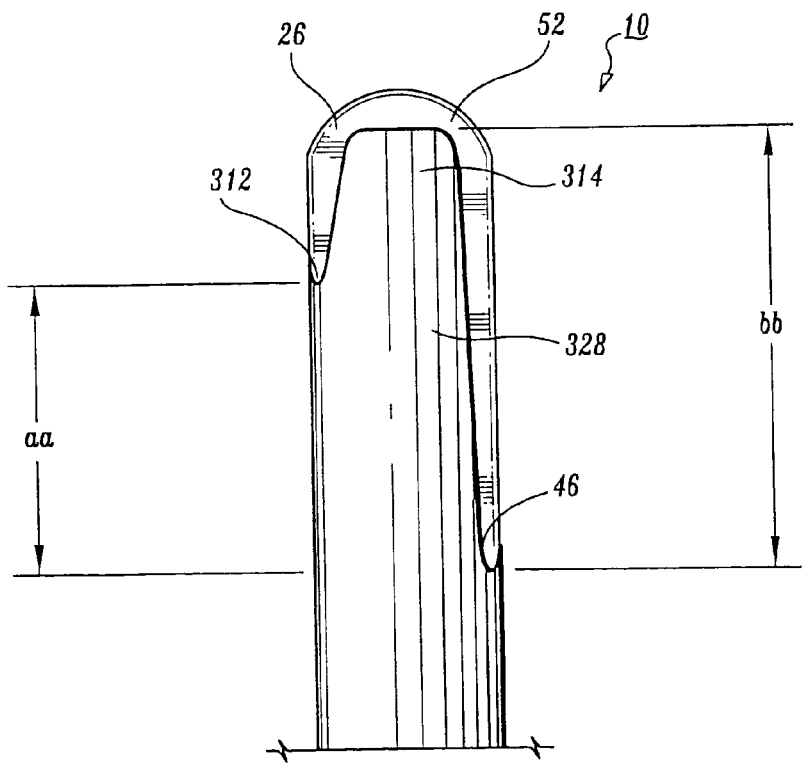
FIG. 15 is an alternate side view of the catheter shown in FIG. 10.
Figure 16:
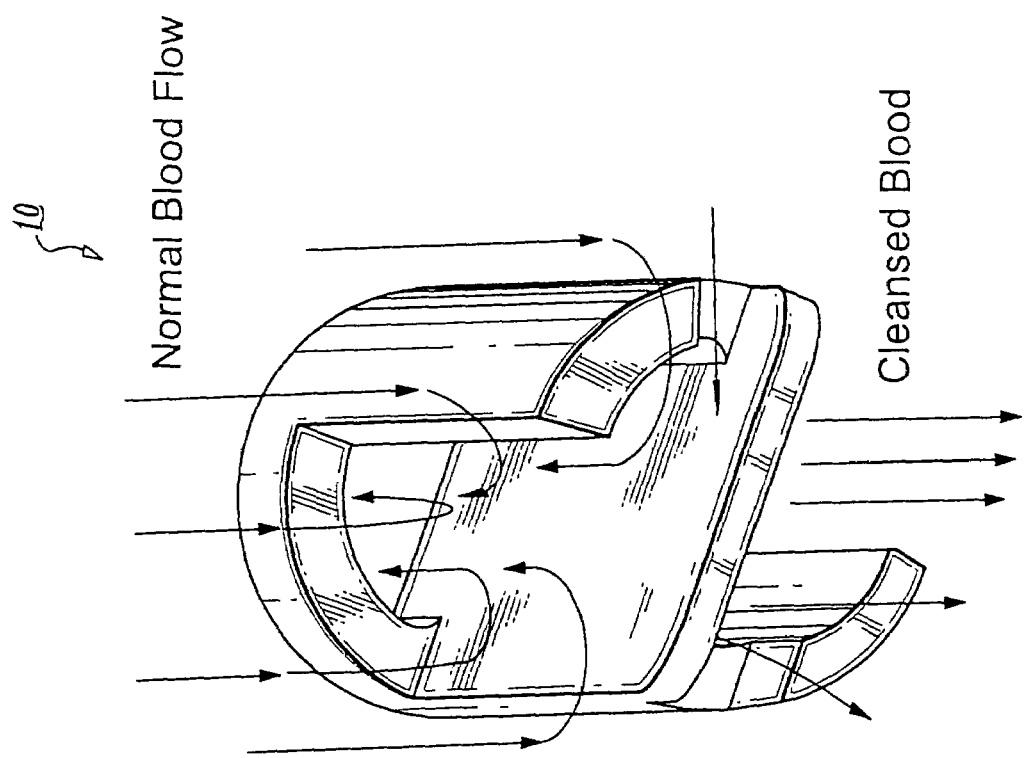
FIG. 16 is a perspective view of the catheter shown in FIG. 10, illustrating fluid flow.
Figure 17:
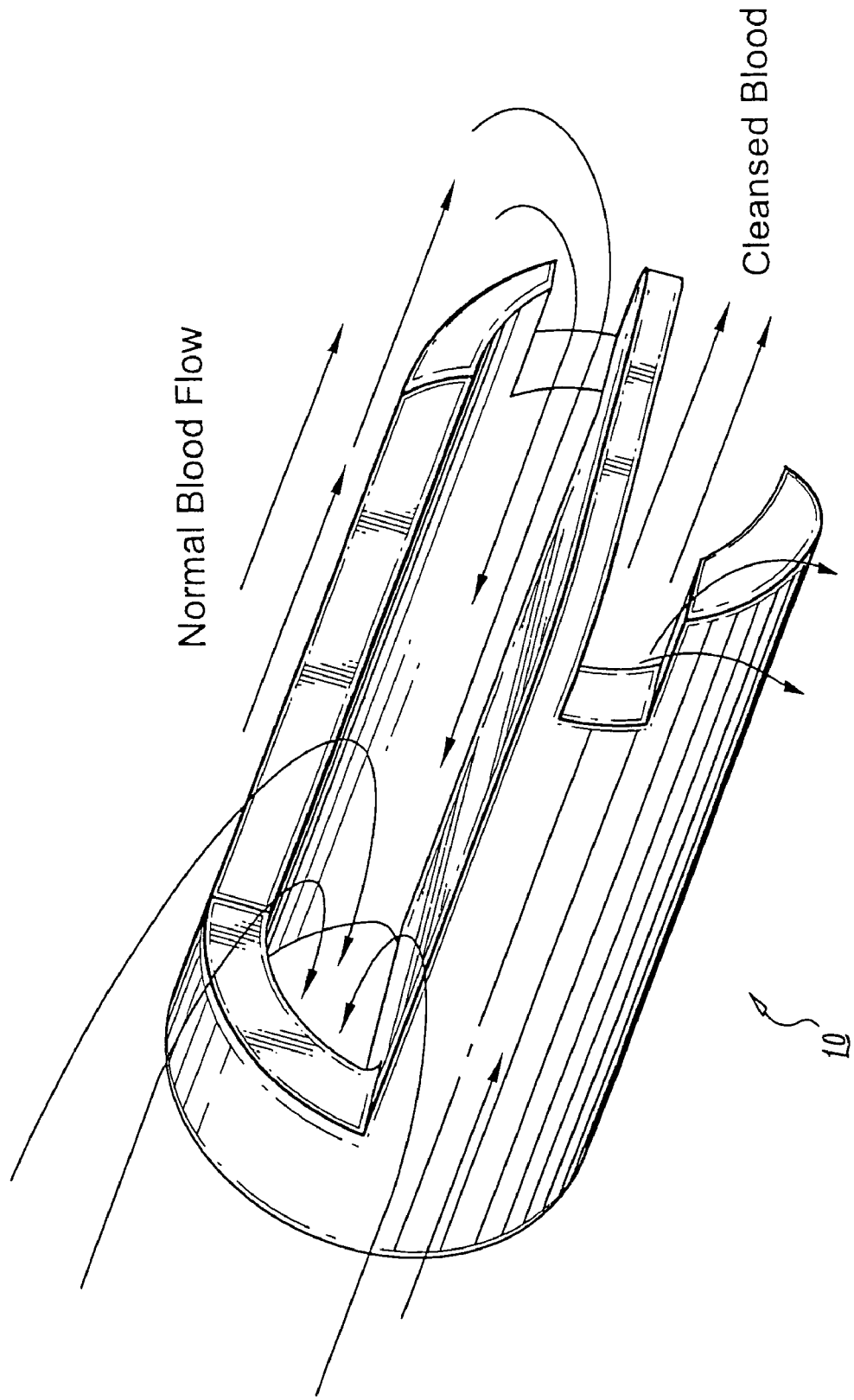
FIG. 17 is a perspective view of the catheter shown in FIG. 10, illustrating fluid flow.
Figure 18:
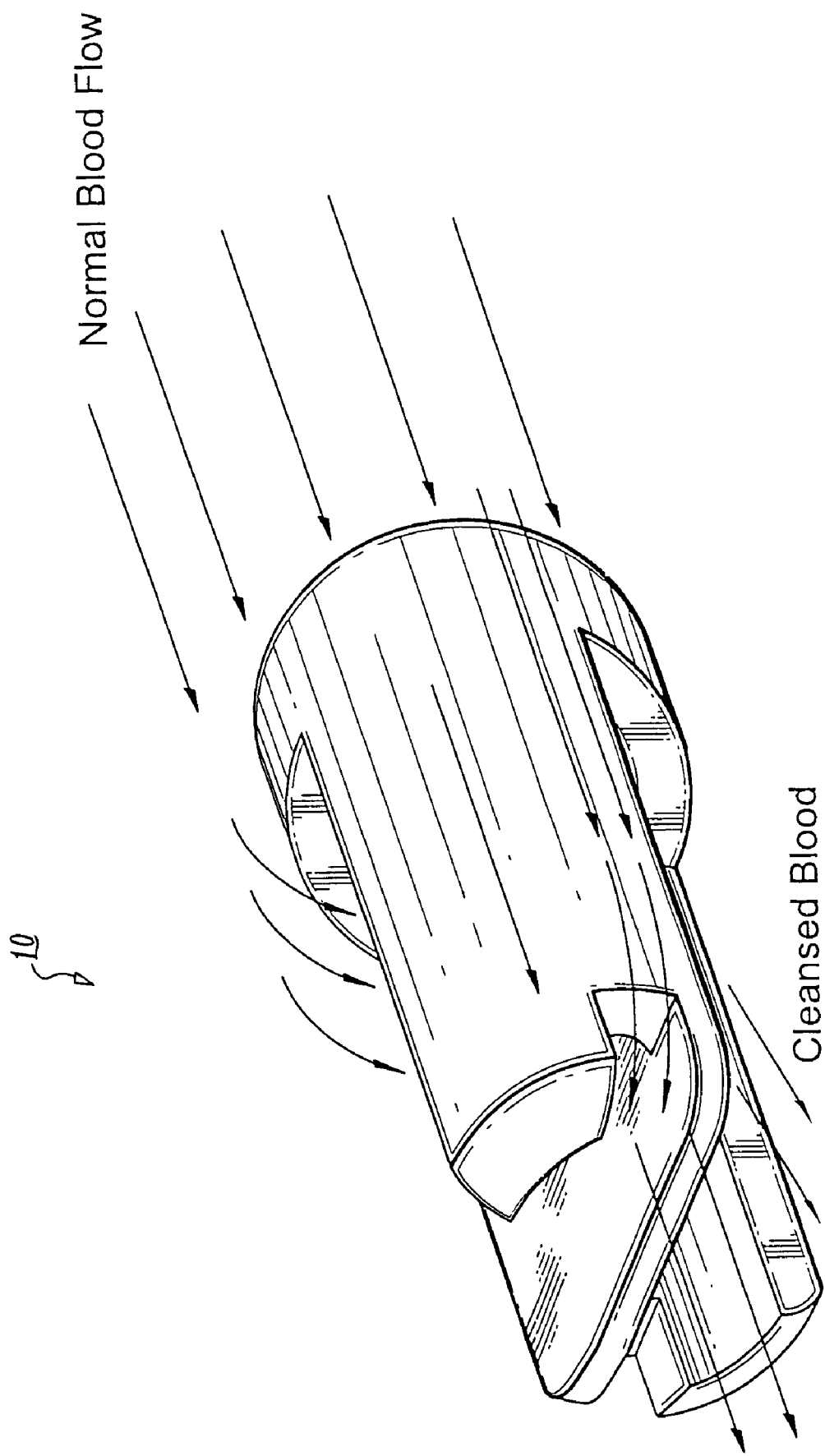
FIG. 18 is a perspective side view of the catheter shown in FIG. 10, illustrating fluid flow.

Concave surface 30 is bounded by a planar end surface 54 of first wall extension 28 and spans a radial distance c. End surface 54 extends about the perimeter of concave surface 30 such that first wall extension 28 has a scoop-like configuration that facilitates fluid flow through first lumen 16. It is contemplated that first wall extension 28 may form alternate configurations, such as, for example, spherical, rectangular, etc. End surface 54 includes a radial portion 55 adjacent a distal end of first wall extension 28. Radial portion 55 extends to the longitudinally oriented outer surface 36 of body 12 in an arcuate configuration. This configuration advantageously prevents a vessel wall (not shown) from becoming disposed within the inlet of first lumen 16. In an alternate embodiment, as shown in FIG. 5, a radial portion 155 extends to the longitudinally oriented outer surface 36 of body 12 in a perpendicular convergence.

It is contemplated that distance c may extend various lengths. Planar end surface 54 is disposed at an angular orientation α relative to first planar surface 52. It is envisioned that end surface 54 may be disposed at various angular orientations α, such as, for example, 5–20 degrees.

Concave surface 30 and first planar surface 52 cooperate to define a first cavity 56. First cavity 56 is disposed distally beyond inlet opening 46. First cavity 56 is dimensioned and configured according to the bounds of one or all of inlet opening 46, concave surface 30, planar end surface 54 and septum extension 26, according to the particular requirements of a catheter application. The extension of first cavity 56 distally beyond inlet opening 46 prevents undesirable recirculation of fluid flow between first lumen 16 and second lumen 18 as facilitated by the barrier provided by septum extension 26.

Second wall extension 32 extends distally, a distance d, beyond outlet opening 50 of second lumen 18 and inlet opening 46 of first lumen 16. It is contemplated that distance d may extend various lengths according to the requirements of a particular catheter application, such as, for example, approximately 0.100–0.200 inches. Concave surface 34 faces a second planar surface 58 of septum extension 26, opposing first planar surface 52, and is spaced apart therefrom a distance e.

It is contemplated that distance e may extend various lengths. It is further contemplated that surface 58 may be non-planar, such as, for example, arcuate, undulating, textured, etc. It is envisioned that surface 52 may be disposed at angular orientations relative to surface 58.

Concave surface 34 is bounded by a planar end surface 60 of second wall extension 32 and spans a radial distance f. End surface 60 extends about the perimeter of concave surface 34 such that second wall extension 32 has a scoop-like configuration that facilitates fluid flow through second lumen 18. It is envisioned that second wall extension 32 may form alternate configurations, such as, for example, spherical, rectangular, etc. End surface 60 includes a radial portion 61 adjacent a distal end of second wall extension 32. Radial portion 61 extends to the longitudinally oriented outer surface 36 of body 12 in an arcuate configuration. This configuration advantageously prevents, for example, a vessel wall (not shown) from becoming disposed within the distal opening of second lumen 18 in the event fluid is reversed and suction is provided for withdrawal of fluid therethrough. In an alternate embodiment, as shown in FIG. 5, a radial portion 161 extends to the longitudinally oriented outer surface 36 in a perpendicular intersection.

It is contemplated that distance f may extend various lengths. Planar end surface 60 is disposed at an angular orientation β relative to second planar surface 58. It is envisioned that end surface 60 may be disposed at various orientations β, such as, for example, 5–20 degrees.

Concave surface 34 and second planar surface 58 cooperate to define a second cavity 62. Second cavity 62 is disposed distally beyond outlet opening 50. Second cavity 62 is dimensioned and configured according to the bounds of one or all of outlet opening 50, concave surface 34, planar end surface 60 and septum extension 26, according to the particular requirements of a catheter application. The extension of second cavity 62 distally beyond outlet opening 50 prevents undesirable recirculation of fluid flow between second lumen 18 and first lumen 16 as facilitated by the barrier provided by septum extension 26.

First wall extension 28 and second wall extension 32 are symmetrically disposed about septum extension 26 such that first cavity 56 and second cavity 62 are symmetrical. First cavity 56 and second cavity 62 bound an equivalent space to facilitate inflow and outflow capability for each lumen. The space bounded by first cavity 56 and second cavity 62 have an angular orientation as facilitated by respective planar end surfaces 54, 60, discussed above. The angular orientations of planar end surfaces 54, 60 (α, β) cause cavities 56, 62 to direct fluid in the direction shown by the arrows in FIG. 4.

The configuration of catheter 10 advantageously facilitates reversible flow between first lumen 16 and second lumen 18 such that, for example, blood clots attaching to catheter 10, including septum 20, may be washed away by alternating blood flow directions. As second lumen 18 expels blood flow for introduction to the body vessel, blood flow is forced out of second lumen 18. The blood flow is axially directed out of cavity 62 past second wall extension 32. It is envisioned that such axially directed blood flow washes away any blood clots disposed adjacent cavity 62. It is further envisioned that fluid flow exiting second lumen 18 may wash other particles undesirably attached to catheter 10. This configuration prevents undesirable recirculation of fluid flow between second lumen 18 and first lumen 16. Thus, blood clots, etc. attached to catheter 10, including septum 20 may be washed away by alternating and/or reversing flow directions with consecutive dialysis. It is contemplated that the alternating and/or reversible flow may be provided by a source outside the body of catheter 10 such as, for example, a dialysis machine, etc. connected thereto.

First lumen 16 is provided with suction to withdraw fluids from the body vessel. Efficiency of fluid inflow through cavity 56 to first lumen 16 is improved due to the configuration of cavity 56 and consequent fluid direction. It is contemplated that blood clots, or other undesired particles, disposed adjacent cavity 56 of first lumen 16 may be washed away by reversing blood flow direction of lumens 16, 18 with consecutive dialysis procedures. Upon reversal of blood flow direction, blood flow is expelled from cavity 56 and the axially directed blood flow washes away blood clots, similar to that described above. Second lumen 18 is provided with suction to withdraw fluids from the body vessel and into opening 50.

The symmetrical configuration of first wall extension 28 and second wall extension 32 supports a vessel wall of a body vessel (not shown). This configuration spaces the vessel wall from inlet opening 46 and outlet opening 50 to prevent vessel wall occlusion of openings 46, 50 during for example, suction through the lumens. It is further envisioned that first wall extension 28 and second wall extension 32 may have sufficient thickness and/or be fabricated from semi-rigid or rigid materials to prevent undesired deformation thereof.

Referring to FIGS. 6–9, another alternate embodiment of catheter 10 is shown, similar to that described above. First wall 22 includes a first wall extension 228 that extends distally beyond first lumen 16 and is spaced apart from septum extension 26. First wall extension 228 defines a concave surface 230 that faces septum extension 26. Second wall 24 includes a second wall extension 232 that extends distally beyond second lumen 18 and is spaced apart from septum extension 26. Second wall extension 32 defines a concave surface 234 that faces septum extension 26.

First wall extension 228 includes a first step 212 and a second step 214 formed therewith. First step 212 is formed with septum extension 26. First step 212 and second step 214 are circumferentially disposed about septum extension 26. It is envisioned that first step 212 and/or second step 214 may have alternate configurations, such as, for example, planar, etc.

First step 212 extends distally, a distance aa, beyond inlet opening 46 of first lumen 16 and outlet opening 50 of second lumen 18. Second step 214 extends distally a distance bb, beyond inlet opening 46 and outlet opening 50. It is contemplated that distance aa and bb may extend various lengths. Concave surface 230 faces first planar surface 52 of septum extension 26 and is spaced apart therefrom. Concave surface 230 spans across approximately one-quarter of the circumference of body 12 or a substantially 90° arc as extended from septum extension 26. It is envisioned that first step 212 and/or second step 214, or other portions of concave surface 230 may be variously disposed about body 12.

Concave surface 230 is bounded by a planar end surface 254 of first wall extension 228. End surface 254 extends about the perimeter of concave surface 230 to facilitate fluid flow through first lumen 16. Concave surface 230 and first planar surface 52 cooperate to define first cavity 56, similar to that described above. First cavity 56 is further bounded by a proximal base 264. Proximal base 264 defines a proximal inlet portion for first lumen 16 during withdrawal of fluids. It is contemplated that suction provided with first lumen 16 has a greater fluid flow rate adjacent proximal base 264.

Second wall extension 232 includes a first step 216 and a second step 218 formed therewith. First step 216 is formed with septum extension 26. First step 216 and second step 218 are circumferentially disposed about septum extension 26. It is contemplated that first step 216 and/or second step 218 may have alternate configurations, such as, for example, planar, etc.

First step 216 extends distally, a distance dd, beyond outlet opening 50 and inlet opening 46. Second step 218 extends distally a distance ee, beyond inlet opening 46 and outlet opening 50. It is contemplated that distances dd and ee may extend various lengths. Concave surface 234 faces second planar surface 58 of septum extension 26, opposing first planar surface 52, and is spaced apart therefrom. Concave surface 234 spans across approximately one-quarter of the circumference of body 12 or a substantially 90° arc, as extended from septum extension 26. It is envisioned that first step 216 and/or second step 218, or other portions of concave surface 234 may be variously disposed about body 12.

Concave surface 234 is bounded by a planar end surface 260 of second wall extension 232. End surface 260 extends about the perimeter of concave surface 234 to facilitate fluid flow through second lumen 18. Concave surface 234 and second planar surface 58 cooperate to define second cavity 62, similar to that described above. Second cavity 62 is further bounded by a proximal base 266. For example, if fluid flow is reversed with catheter 10, proximal base 266 defines a proximal inlet portion for second lumen 18 during withdrawal of fluids. It is contemplated that suction provided with second lumen 18 has a greater fluid flow rate adjacent proximal base 266.

First wall extension 228 and second wall extension 232 are symmetrically disposed about septum extension 26 such that first cavity 56 and second cavity 62 are symmetrical. First cavity 56 and second cavity 62 bound an equivalent space to facilitate inflow and outflow capability for each lumen.

The configuration of catheter 10 advantageously facilitates reversible flow between first lumen 16 and second lumen 18 such that, for example, blood clots attaching to catheter 10 may be washed away by alternating blood flow directions. As second lumen 18 expels blood flow for introduction to the body vessel, blood flow is forced out of second lumen 18.

The blood flow is axially directed out of cavity 62 past second wall extension 232. It is envisioned that such axially directed blood flow washes away any blood clots disposed adjacent cavity 62. It is further envisioned that fluid flow exiting second lumen 18 may wash other particles undesirably attached to catheter 10.

First lumen 16 is provided with suction to withdraw fluids from the body vessel. The suction draws blood flow from various directions and orientations into inlet opening 46. Suction is greater adjacent proximal base 264 due to its closer proximity to a suction source (not shown). Fluid flow is greater adjacent to proximal base 264 and therefore, advantageously disposed proximal to the blood flow being expelled from cavity 62 of second lumen 18. This configuration minimizes recirculation between lumens 16, 18.

It is contemplated that blood clots, or other undesired particles, disposed adjacent cavity 56 of first lumen 16 may be washed away by reversing blood flow direction of lumens 16, 18. Upon reversal of blood flow direction, blood flow is expelled from cavity 56 and the axially directed blood flow washes away blood clots, similar to that described above.

Second lumen 18 is provided with suction to withdraw fluids from the body vessel and into opening 50. Second wall extension 232 is symmetrical with first wall extension 228, and therefore, similar to proximal base 264, suction is greater adjacent proximal base 266. Fluid flow is greater adjacent to proximal base 266 and therefore, advantageously disposed proximal to the blood flow being expelled from cavity 56. This configuration minimizes recirculation between lumens 16, 18.

Referring to FIGS. 10–18, another alternate embodiment of catheter 10 is shown, similar to that described above. First wall 22 includes a first wall extension 328 that extends distally beyond first lumen 16 and is spaced apart from septum extension 26. First wall extension 328 defines a concave surface 330 that faces septum extension 26. Second wall 24 includes a second wall extension 332 that extends distally beyond second lumen 18 and is spaced apart from septum extension 26. Second wall extension 32 defines a concave surface 334 that faces septum extension 26.

First wall extension 328 includes a first step 312 and a second step 314 formed therewith in an arcuate transition. First step 312 is formed with septum extension 26 in an arcuate transition. First step 312 and second step 314 are circumferentially disposed about septum extension 26. It is envisioned that first step 312 and/or second step 314 may have alternate configurations, such as, for example, planar, etc.

First step 312 extends distally, a distance aa, beyond inlet opening 46 of first lumen 16 and outlet opening 50 of second lumen 18. Second step 314 extends distally a distance bb, beyond inlet opening 46 and outlet opening 50. It is contemplated that distance aa and bb may extend various lengths. Concave surface 330 faces first planar surface 52 of septum extension 26 and is spaced apart therefrom. Concave surface 330 spans across approximately one-quarter of the circumference of body 12 or a substantially 90° arc as extended from septum extension 26. It is envisioned that first step 312 and/or second step 314, or other portions of concave surface 330 may be variously disposed about body 12.

Concave surface 330 is bounded by a planar end surface 354 of first wall extension 328. End surface 354 extends about the perimeter of concave surface 330 to facilitate fluid flow through first lumen 16. Concave surface 330 and first planar surface 52 cooperate to define first cavity 56, similar to that described above. First cavity 56 is further bounded by a proximal base 364. Proximal base 364 has an arcuate configuration and defines a proximal inlet portion for first lumen 16 during withdrawal of fluids. It is contemplated that suction provided with first lumen 16 has a greater fluid flow rate adjacent proximal base 364.

Second wall extension 332 includes a first step 316 and a second step 318 formed therewith in an arcuate transition. First step 316 is formed with septum extension 26. First step 316 and second step 318 are circumferentially disposed about septum extension 26. It is contemplated that first step 316 and/or second step 318 may have alternate configurations, such as, for example, planar, etc.

First step 316 extends distally, a distance dd, beyond outlet opening 50 and inlet opening 46. Second step 318 extends distally a distance ee, beyond inlet opening 46 and outlet opening 50. It is contemplated that distances dd and ee may extend various lengths. Concave surface 334 faces second planar surface 58 of septum extension 26, opposing first planar surface 52, and is spaced apart therefrom. Concave surface 334 spans across approximately one-quarter of the circumference of body 12 or a substantially 90° arc, as extended from septum extension 26. It is envisioned that first step 316 and/or second step 318, or other portions of concave surface 334 may be variously disposed about body 12.

Concave surface 334 is bounded by a planar end surface 360 of second wall extension 332. End surface 360 extends about the perimeter of concave surface 334 to facilitate fluid flow through second lumen 18. Concave surface 334 and second planar surface 58 cooperate to define second cavity 62, similar to that described above. Second cavity 62 is further bounded by a proximal base 366. For example, if fluid flow is reversed with catheter 10, proximal base 366 has an arcuate configuration and defines a proximal inlet portion for second lumen 18 during withdrawal of fluids. It is contemplated that suction provided with second lumen 18 has a greater fluid flow rate adjacent proximal base 366.

First wall extension 328 and second wall extension 332 are symmetrically disposed about septum extension 26 such that first cavity 56 and second cavity 62 are symmetrical. First cavity 56 and second cavity 62 bound an equivalent space to facilitate inflow and outflow capability for each lumen.

The configuration of catheter 10 advantageously facilitates reversible flow between first lumen 16 and second lumen 18 by alternating blood flow directions. As second lumen 18 expels blood flow for introduction to the body vessel, blood flow is forced out of second lumen 18. The blood flow is axially directed out of cavity 62 past second wall extension 332. It is envisioned that such axially directed blood flow washes away any blood clots disposed adjacent cavity 62.

First lumen 16 is provided with suction to withdraw fluids from the body vessel. The suction draws blood flow from various directions and orientations into inlet opening 46. Suction is greater adjacent proximal base 364 due to its closer proximity to a suction source (not shown). Fluid flow is greater adjacent to proximal base 364 and therefore, advantageously disposed proximal to the blood flow being expelled from cavity 62 of second lumen 18. This configuration minimizes recirculation between lumens 16, 18.

It is contemplated that blood clots, or other undesired particles, disposed adjacent cavity 56 of first lumen 16 may be washed away by reversing blood flow direction of lumens 16, 18. Upon reversal of blood flow direction, blood flow is expelled from cavity 56 and the axially directed blood flow washes away blood clots, similar to that described above.

Second lumen 18 is provided with suction to withdraw fluids from the body vessel and into opening 50. Second wall extension 332 is symmetrical with first wall extension 328, and therefore, similar to proximal base 364, suction is greater adjacent proximal base 366. Fluid flow is greater adjacent to proximal base 366 and therefore, advantageously disposed proximal to the blood flow being expelled from cavity 56. This configuration minimizes recirculation between lumens 16, 18.

Figure 19:
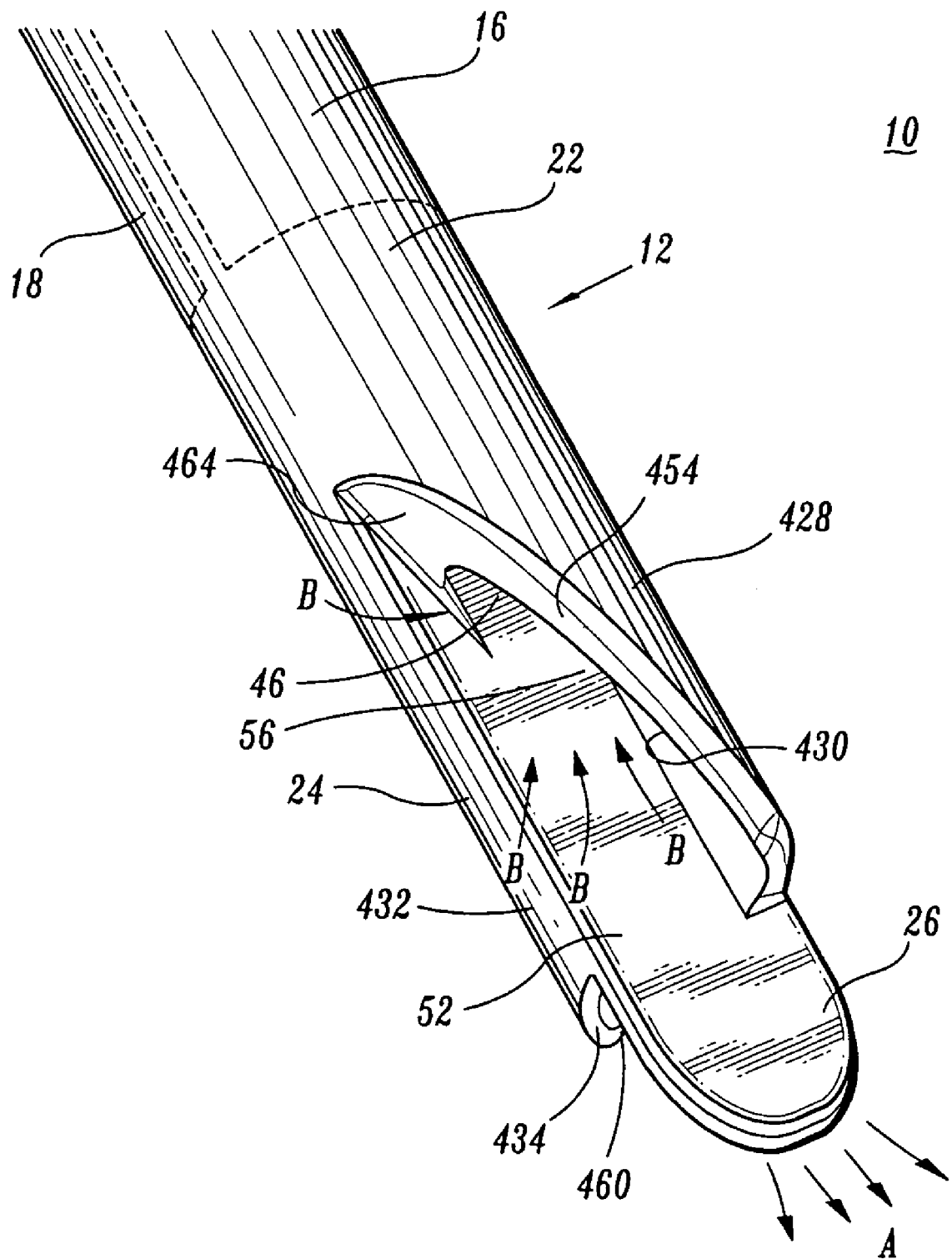
FIG. 19 is a perspective view of another alternate embodiment of the catheter shown in FIG. 1.
Figure 20:
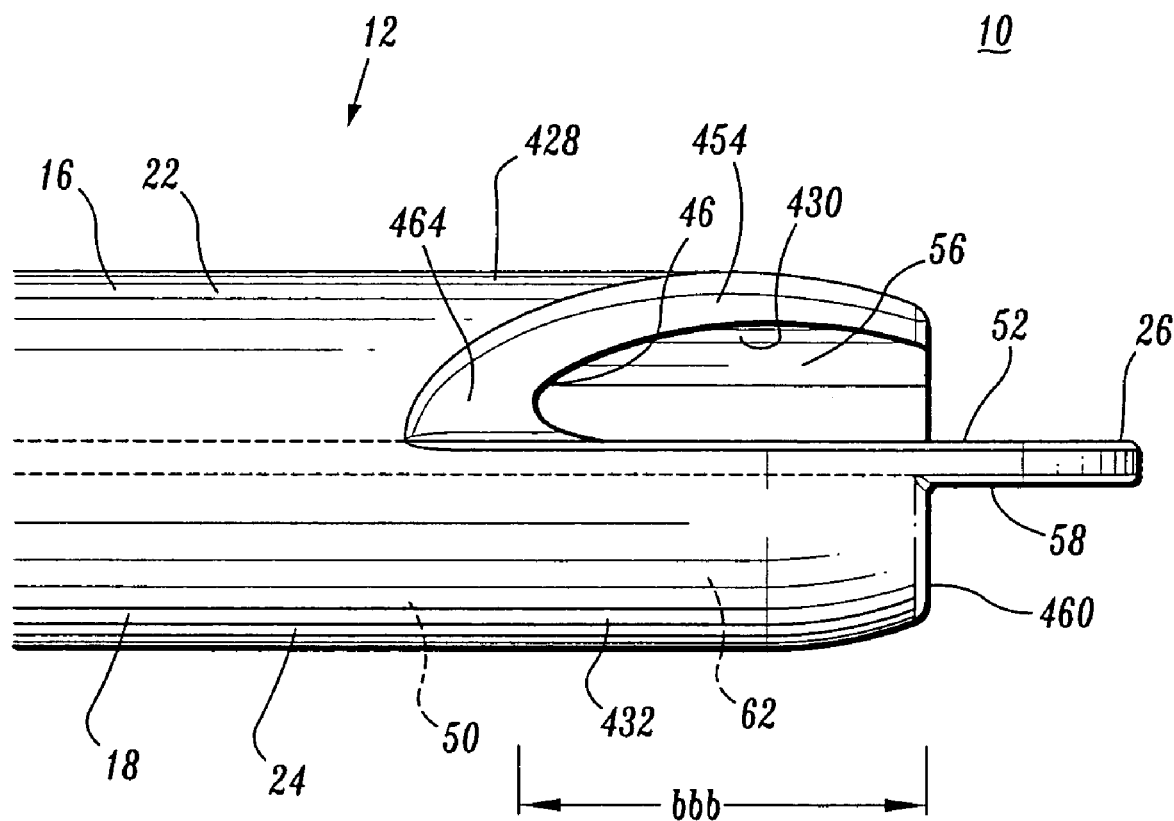
FIG. 20 is a side view of the catheter shown in FIG. 19.
Figure 21:
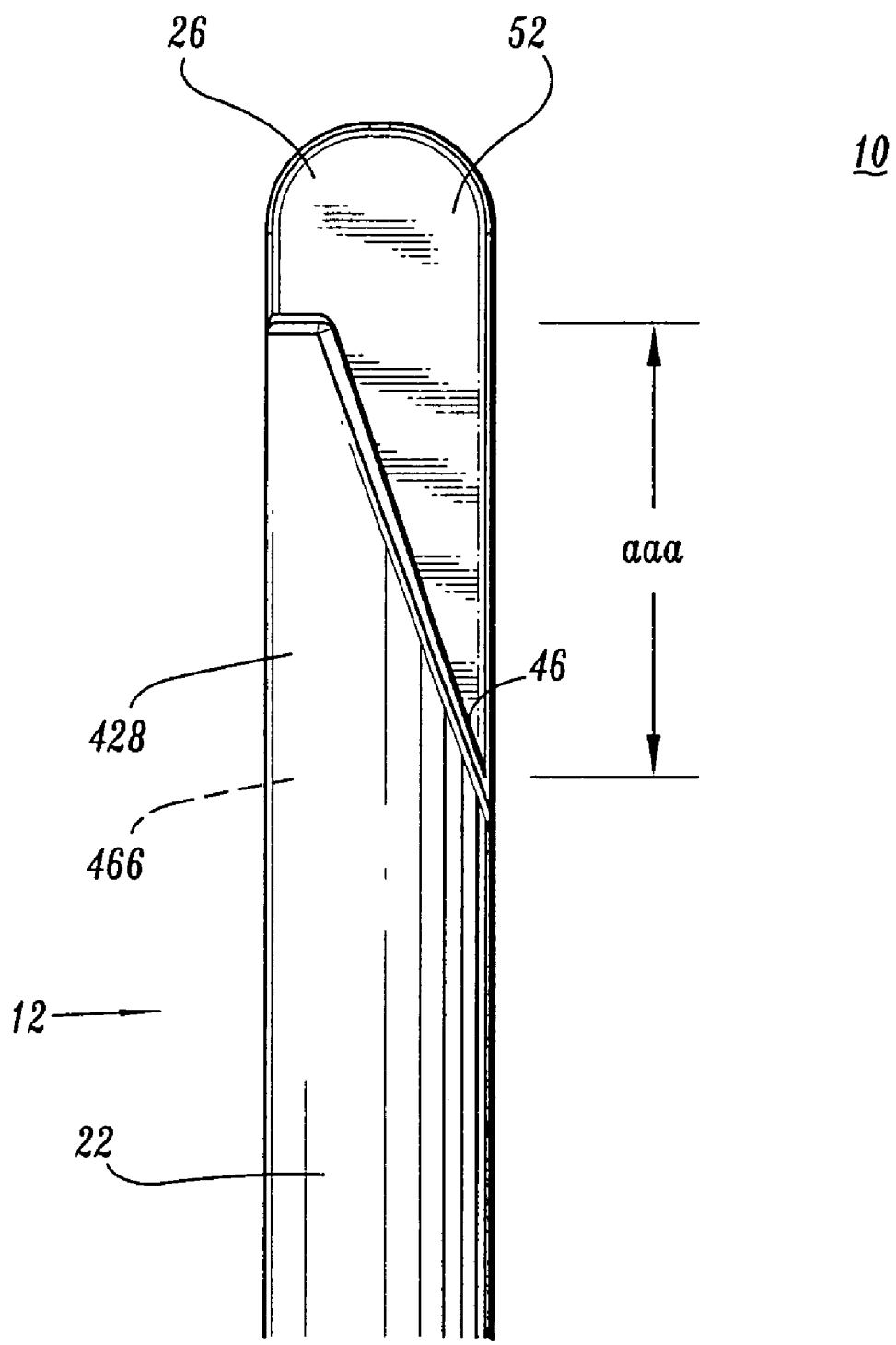
FIG. 21 is an alternate side view of the catheter shown in FIG. 19.

Referring to FIGS. 19–21, another alternate embodiment of catheter 10 is shown, similar to that described above. First wall 22 includes a first wall extension 428 that extends distally beyond first lumen 16 and is spaced apart from septum extension 26. First wall extension 428 defines a concave surface 430 that faces septum extension 26. Second wall 24 includes a second wall extension 432 that extends distally beyond second lumen 18 and is spaced apart from septum extension 26. Second wall extension 432 defines a concave surface 434 that faces septum extension 26.

First wall extension 428 is circumferentially disposed about septum extension 26 in a spiral configuration to facilitate fluid flow and prevent recirculation between lumens 16,18. It is envisioned that first wall extension 428 may include various spiral configurations, such as, for example, a more elongated spiral, a spiral having a more acute winding type design, helical, etc. First wall extension 428 extends distally, a distance aaa, beyond inlet opening 46 of first lumen 16 and outlet opening 50 (shown in phantom) of second lumen 18. It is contemplated that distance aaa may extend various lengths. Concave surface 430 faces first planar surface 52 of septum extension 26 and is spaced apart therefrom.

Concave surface 430 is bounded by a planar end surface 454 of first wall extension 428. End surface 454 extends about the perimeter of concave surface 430 in a spiral configuration, as described above, to facilitate fluid flow through first lumen 16. Concave surface 430 and first planar surface 52 cooperate to define first cavity 56, similar to that described above. First cavity 56 is further bounded by a proximal base 464 of end surface 454. Proximal base 464 is formed with septum extension 26 in an arcuate transition. Proximal base 464 has an arcuate configuration and defines a proximal inlet portion for first lumen 16 during withdrawal of fluids. It is contemplated that suction provided with first lumen 16 has a greater fluid flow rate adjacent proximal base 464.

Second wall extension 432 is circumferentially disposed about septum extension 26 in a spiral configuration to facilitate fluid flow and prevent recirculation between lumens 16,18. It is envisioned that first wall extension 432 may include various spiral configurations, such as, for example, a more elongated spiral, a spiral having a more acute winding type design, helical, etc. Second wall extension 432 extends distally, a distance bbb, beyond outlet opening 50 (shown in phantom and similarly configured to inlet opening 46) and inlet opening 46. It is contemplated that distance bbb may extend various lengths. Concave surface 434 faces second planar surface 58, opposing first planar surface 52, of septum extension 26 and is spaced apart therefrom.

Concave surface 434 is bounded by a planar end surface 460 of second wall extension 432. End surface 460 (similarly configured to end surface 454, although end surfaces 454,460 may include alternative or distinct structure) extends about the perimeter of concave surface 434 in a spiral configuration, as described above, to facilitate fluid flow through second lumen 18. Concave surface 434 and second planar surface 58 cooperate to define second cavity 62 (shown in phantom), similar to that described above. Second cavity 62 is further bounded by a proximal base 466 of end surface 460 (shown in phantom and similarly configured to base 464, although bases 464,466 may include alternative or distinct structure). For example, if fluid flow is reversed with catheter 10, proximal base 466 has an arcuate configuration and defines a proximal inlet portion for second lumen 18 during withdrawal of fluids. It is contemplated that suction provided with second lumen 18 has a greater fluid flow rate adjacent proximal base 466.

First wall extension 428 and second wall extension 432 are symmetrically disposed about septum extension 26 such that first cavity 56 and second cavity 62 are symmetrical. First cavity 56 and second cavity 62 bound an equivalent space to facilitate inflow and outflow capability for each lumen.

The configuration of catheter 10 advantageously facilitates reversible flow between first lumen 16 and second lumen 18 by alternating blood flow directions. As second lumen 18 expels blood flow for introduction to the body vessel (shown by arrows A in FIG. 19), blood flow is forced out of second lumen 18. The blood flow is axially directed out of cavity 62 past second wall extension 432. It is envisioned that such axially directed blood flow washes away any blood clots disposed adjacent cavity 62.

First lumen 16 is provided with suction to withdraw fluids from the body vessel. The suction draws blood flow from various directions and orientations into inlet opening 46 (shown by arrows B in FIG. 19). Suction is greater adjacent proximal base 464 due to its closer proximity to a suction source (not shown). Fluid flow is greater adjacent to proximal base 464 and therefore, advantageously disposed proximal to the blood flow being expelled from cavity 62 of second lumen 18. This configuration minimizes recirculation between lumens 16, 18.

It is contemplated that blood clots, or other undesired particles, disposed adjacent cavity 56 of first lumen 16 may be washed away by reversing blood flow direction of lumens 16, 18. Upon reversal of blood flow direction, blood flow is expelled from cavity 56 and the axially directed blood flow washes away blood clots, similar to that described above.

Second lumen 18 is provided with suction to withdraw fluids from the body vessel and into opening 50. Second wall extension 432 is symmetrical with first wall extension 428, and therefore, similar to proximal base 464, suction is greater adjacent proximal base 466. Fluid flow is greater adjacent to proximal base 466 and therefore, advantageously disposed proximal to the blood flow being expelled from cavity 56. This configuration minimizes recirculation between lumens 16, 18.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A catheter comprising:
    an elongated tubular body defining a longitudinal axis and extending to a distal end thereof, the tubular body having a first lumen and a second lumen with a septum disposed therebetween, the tubular body including a first wall that defines the first lumen and a second wall that defines the second lumen, a portion of the septum extending distally beyond the first lumen and the second lumen;
    wherein the first wall includes a first wall extension that extends in a spiral configuration from the first lumen about the longitudinal axis and is spaced apart from the portion of the septum.

2. A catheter as recited in claim 1, wherein the second wall includes a second wall extension that extends in a spiral configuration from the second lumen and is spaced apart from the portion of the septum.

3. A catheter as recited in claim 1, wherein the first wall extension includes a planar end surface that forms a boundary about the first wall extension and defines the spiral configuration of the first wall extension.

4. A catheter as recited in claim 2, wherein the second wall extension includes a planar end surface that forms a boundary about the second wall extension and defines the spiral configuration of the second wall extension.

5. A catheter as recited in claim 2, wherein the first wall extension defines a first cavity and the second wall extension defines a second cavity, the first cavity and the second cavity being symmetrical.

6. A catheter as recited in claim 2, wherein the first wall extension and the second wall extension are symmetrically disposed about the portion of the septum.

7. A catheter as recited in claim 5, wherein the first wall extension includes a base that defines an inlet opening of the first cavity, the base being disposed proximal to fluid flow being expelled from the second cavity of the second wall extension.

8. A catheter comprising:
    an elongated tubular body defining a longitudinal axis and extending to a distal tip and having a septum that separates a first lumen and a second lumen thereof, the tubular body including a first wall that defines the first lumen and a second wall that defines the second lumen, the septum having a septum extension disposed adjacent the distal tip and extending distally beyond the first lumen and the second lumen, wherein the first wall includes a first wall extension that extends distally beyond the first lumen in a spiral configuration about the longitudinal axis and is spaced apart from the septum extension, the first wall extension defining a concave surface facing the septum extension, the second wall including a second wall extension that extends distally beyond the second lumen in a spiral configuration and is spaced apart from the septum extension, the second wall extension defining a concave surface facing the septum extension.

9. A catheter as recited in claim 8, wherein the first wall extension and the second wall extension each include planar end surfaces that form a boundary about their respective concave surfaces and define the spiral configuration of the respective first and second wall extensions.

10. A catheter as recited in claim 8, wherein the concave surface of the first wall extension defines a first cavity and the concave surface of the second wall extension defines a second cavity, the first cavity and the second cavity being symmetrical.

11. A catheter as recited in claim 10, wherein the first wall extension includes a first base that defines an inlet opening of the first cavity, the first base being disposed proximal to fluid flow being expelled from the second cavity of the second wall extension and the second wall extension includes a second base that defines an inlet opening of the second cavity, the second base being disposed proximal to fluid flow being expelled from the first cavity of the second wall extension.

12. A catheter as recited in claim 8, wherein the first wall extension and the second wall extension are symmetrically disposed about the septum extension.

13. A catheter comprising:

an elongated tubular body defining a longitudinal axis and extending to a distal end and having a septum that separates a first lumen and a second lumen thereof, the tubular body including a first wall that defines the first lumen and a second wall that defines the second lumen, the septum having a septum extension disposed adjacent the distal end and extending distally beyond the first lumen and the second lumen, the first wall includes a first wall extension that extends distally beyond the first lumen in a spiral configuration about the longitudinal axis and is spaced apart from the septum extension, the second wall including a second wall extension that extends distally beyond the second lumen in a spiral configuration and is spaced apart from the septum extension, wherein the first wall extension defines a first cavity and the second wall extension defines a second cavity, the first wall extension includes a first base that defines an inlet opening of the first cavity, the first base being disposed proximal to fluid flow being expelled from the second cavity of the second wall extension.

14. A catheter as recited in claim 13, wherein the second wall extension includes a second base that defines an inlet opening of the second cavity, the second base being disposed proximal to fluid flow being expelled from the first cavity of the second wall extension.

15. A catheter as recited in claim 13, wherein the first base has an arcuate configuration.

16. A catheter as recited in claim 14, wherein the second base has an arcuate configuration.

17. A catheter as recited in claim 13, wherein the first cavity and the second cavity are symmetrical.

18. A catheter as recited in claim 13, wherein the first wall extension defines a concave surface facing the septum extension.

19. A catheter as recited in claim 13, wherein the second wall extension defines a concave surface facing the septum extension.

* * * * *